(12) United States Patent
Christoph et al.

(10) Patent No.: US 8,422,624 B2
(45) Date of Patent: Apr. 16, 2013

(54) METHOD AND APPARATUS FOR DIMENSIONALLY MEASURING BY MEANS OF COORDINATE MEASURING INSTRUMENTS

(75) Inventors: Ralf Christoph, Giessen (DE); Wolfgang Rauh, Lahntal (DE); Michael Hammer, Reiskirchen (DE)

(73) Assignee: Werth Messtechnik GmbH, Giessen (DE)

( * ) Notice: Subject to any disclaimer, the term of this patent is extended or adjusted under 35 U.S.C. 154(b) by 765 days.

(21) Appl. No.: 12/596,031

(22) PCT Filed: Apr. 18, 2008

(86) PCT No.: PCT/EP2008/054699
§ 371 (c)(1),
(2), (4) Date: Oct. 28, 2009

(87) PCT Pub. No.: WO2008/128978
PCT Pub. Date: Oct. 30, 2008

(65) Prior Publication Data
US 2010/0145653 A1 Jun. 10, 2010

(30) Foreign Application Priority Data

Apr. 20, 2007 (DE) .......................... 10 2007 019 148
May 7, 2007 (DE) .......................... 10 2007 021 809

(51) Int. Cl.
*G01N 23/00* (2006.01)

(52) U.S. Cl.
USPC .............................................. 378/4

(58) Field of Classification Search ................ 378/4, 19, 378/23, 51; 702/152, 95
See application file for complete search history.

(56) References Cited

U.S. PATENT DOCUMENTS

| | | | |
|---|---|---|---|
| 2004/0066908 A1* | 4/2004 | Hanke et al. .................. | 378/901 |
| 2004/0172215 A1 | 9/2004 | Russell | |
| 2005/0163278 A1* | 7/2005 | Metz et al. ........................ | 378/4 |
| 2008/0075227 A1 | 3/2008 | Cristoph | |

FOREIGN PATENT DOCUMENTS

GB 2194367 3/1988

* cited by examiner

*Primary Examiner* — Irakli Kiknadze
(74) *Attorney, Agent, or Firm* — Ladas & Parry LLP (57) ABSTRACT

A method and an apparatus for dimensionally measuring parts by means of a coordinate measuring instrument. In order enable measurement of parts that are made of different materials with great accuracy, a computerized tomography sensor is integrated into the coordinate measuring instrument.

36 Claims, 6 Drawing Sheets

METHOD AND APPARATUS FOR DIMENSIONALLY MEASURING BY MEANS OF COORDINATE MEASURING INSTRUMENTS

The invention relates to a method and a device for dimensional measurement with coordinate measuring devices.

Coordinate measuring devices with various sensors used to measure the geometry of workpieces are known. Optical and tactile sensors have been described as such sensors (DE.Z.: Die Bibliothek der Technik, Vol. 248). It is also known to use computer tomography apparatuses for the determination of workpiece geometries, particularly imperfections. Thus, DE-A-103 31 419 discloses a combination of the two devices. Here a computer tomography apparatus is attached firmly to the basic body of the coordinate measuring device. The position of the measured object is here determined using conventional sensor systems used in the coordinate measurement technology, and then the measured object is positioned in the measurement area of the computer tomography apparatus.

From DE-A-100 44 169, a method for determining the thickness of workpieces is known. Here, X-ray radiation permeating the measured component hits a detector. The component can be rotated as well as raised and lowered by means of a manipulator. After complete transillumination of the component, a computer of a computer tomography apparatus delivers a stack of gray value section images which are assembled to obtain a three-dimensional voxel data set. From the latter, the wall thickness of the component is then calculated.

From DE-C-38 06 686, a coordinate measuring device with a multisensor sensor system is known, which comprises a tactile sensor, a laser sensor, and a video sensor, where one of these sensors is used depending on the measurement tasks. In EP-A-1 389 263, one of these sensors is replaced by a computer tomography apparatus.

From US-A-2003/0043964, an inspection system for aircraft hulls is known, which comprises an X-ray source that originates within the hull from a crane, and a sensor, also originating from a crane, outside of the hull. To determine the position of the sensor, a triangulation method is used.

A measuring device according to DE-A-100 01 239 provides, besides a position detector, a non-optical measurement system, such as, an AFM (Atomic Force Microscope), the two being connected rigidly by a support element.

A multisensor measurement head according to DE-A-44 45 331 comprises a vertical axle, on which several sensors can be mounted.

In a coordinate measuring device according to EP-A-0 504 609, joint milling heads are used, besides measurement heads.

An X-ray test arrangement according to U.S. Pat. No. 5,038,378 provides for the possibility of adjusting an X-ray detector independently of each other along three axes.

From WO-A-2005/119174, a coordinate measuring device is known, in which a measurement is carried out with an X-ray sensor system and also with a second sensor system, each in an equivalent arrangement in the coordinate measuring device. Here, the possibility exists that, due to the measurement with other sensors, such as, tactile sensors, data that result from the tomography can be corrected to increase the accuracy. In the corresponding state of the art, workpieces can be measured even they present low contrast with respect to X-ray radiation. To achieve this, the corresponding object is surrounded by a material that presents a higher absorption than the object itself.

The measurement of parts made of different materials is problem that has remained unsolved, or has been solved only unsatisfactorily. Such materials can be measured only poorly or not at all using the conventional methods of tomography. For example, this difficulty is encountered in measuring parts where a metal, for example, steel, is embedded in plastic. Tomography here allows indeed the measurement of the enclosed metal core. However, due to the very high setting of the radiation that is used for this purpose, a simultaneous measurement of the plastic jacket can be carried out only with low precision or not at all, because of the low contrast.

The problem of the present invention is to further develop a method as well as a device for dimensional measurement with coordinate measuring devices, in which a computer tomography sensor is integrated, in such a way that parts that are made of different materials can be measured with high accuracy, particularly parts where heavy materials, such as, metals, and light materials, such as, plastic, are embedded.

The solution of this problem is given in the measures that can be obtained from the claims. Here, the characteristics themselves which can be obtained from the claims are in principle inventive, even if the formulation might result in a potential mutual dependency.

The problem that is the basis of the invention is solved substantially by measuring, in addition to the measurement with tomography, a second point cloud with another sensor, particularly a laser line sensor. Alternatively to the laser line sensor, it is also possible to use tactile sensors, strip projection sensors or other sensors that are capable of probing the surface of the material and are suitable for coordinate measuring devices. By the superposition of the computer tomography measurement data of the heavy core, such as, a metal core, and the measurement data of the surface, which are determined with the alternative sensor, an overall measurement result is obtained for the part that has a combination of materials. Thus, it is possible to combine the advantage of measuring internal geometries by means of computer tomography with the advantage of the precise measurement of external geometries using conventional sensors of the coordinate measurement technology.

The usability of coordinate measuring devices that are suitable for measuring many points, for example, with computer tomography or a laser line sensor system, can be extended by an appropriate point selection, and connection of the measurement system with CAD data. One can, for example, implement in the software the capacity for the user to select a patch in the CAD model. Appropriate software algorithms select automatically all the points of the measured object that are associated geometrically with this patch, and determined by tomography or another sensor system. From this, the actual measurement result of the object to be measured is determined (such as, plane, cylinder surface).

An alternative path here consists in pointing to a point of the point cloud by operating the mouse. If the target geometry element (plane, cylinder surface or similar element) has been selected beforehand, neighboring points are selected and added by the software as often as needed, until the shape deviation of a continuously calculated compensation element (such as, plane, cylinder surface) exceeds a predetermined limit value. In this way it is possible to select all the measuring points that are to be assigned to the previously selected regular geometric element (such as, plane, cylinder surface). From this, the measurement result is determined and issued.

An additional method for improving the performance capacity of multisensor coordinate measuring devices with computer tomography consists in determining correction values for the correction of the tomographic measurement result to correct systematic errors in the tomography, in an additional part of the measurement using alternate sensors, for example, tactile sensors. For this purpose, for all the points measured by tactile means, the deviation between the tomography measurement result and the tactile measurement result is determined and stored. In the measurement of an additional part by means of tomography, this deviation can be superposed at the given place as correction values over the tomography measurement result, and thus a corrected measurement result can be determined. In the context of program technology, it is particularly advantageous here to assign the correction values to all the measuring points to be measured by tactile means, and then reproduce, during the automatic measurement on the computer tomography clouds, the tactile measurement on the tomography point cloud, taking into account the correction values. This means that a calculation of the measurement is carried out, from the currently tomographed measuring points at the place where the sensing with contact is to occur during tactile measurement, by calculating several points in the neighborhood of the tomography point cloud, and adding the previously determined deviation value.

In particular, it is provided for the measurement to occur within the structures of the component to be measured, particularly metal structures, by computer tomography, while the measurement of the component surface occurs entirely or partially by optical or tactile sensors, particularly laser line sensors, and for the measurement results of both sensors to be evaluated finally in a coordinate system.

Here, the sensors used, that is computer tomography sensor and the optical or tactile or laser line sensors, can be calibrated mutually with respect to the calibration range.

It is preferred for the point clouds measured with tomography and a tactile or optical sensor to be mutually aligned respectively superposed using optical overlap of shared geometric characteristics, so that the measurement within a coordinate system becomes possible.

In the process, the measuring points to be selected for the measurement are selected by the user by the selection of CAD patches.

This must be considered an inventive idea, just like the solution proposal that the CAD model of the measured object and the measured point cloud be made to overlap by BestFit or manual adaptation.

In particular, all the measuring points that are located within a search area about the selected CAD patch are used for further evaluation.

In the process, in case of the selection of an individually measured point, additional points can be automatically selected and added.

Another equally specific teaching according to the invention is that, prior to the selection of a point, a regular geometric element, such as, a cylinder/plane, is selected as target element, and then as many measuring points are selected by the software as are needed, until the shape deviation of a compensation element of the type of the target element, which is calculated from the selected points, in its shape deviation falls below a previously established limit value.

Before the selection of a point, a cylinder can be selected as regular geometric target, and then as many measuring points are selected by the software as are needed, until the shape deviation of a compensation element, which is calculated from the selected points, in its shape deviation falls below a previously established limit value.

In addition, it is possible, prior to the selection of a point, to select a plane as regular geometric target element, and then as many measuring points are selected by the software as are needed, until the shape deviation of a compensation element, which is calculated from the selected points, in its shape deviation falls below a previously established limit value.

Alternatively or complementary, it is possible, prior to the selection of a point, to select a sphere as regular geometric target element, and then as many measuring points are selected by the software as are needed, until the shape deviation of a compensation element, which is calculated from the selected points, in its shape deviation falls below a previously established limit value.

An additional possibility is that, prior to the selection of a point, a torus is selected as regular geometric target element, and then as many measuring points are selected by the software as are needed, until the shape deviation of a compensation element, which is calculated from the selected points, in its shape deviation falls below a previously established limit value.

There is also the possibility to select, prior to the selection of a point, a target element in the form of a free form patch described in the CAD format, and then as many measuring points are selected by the software as are needed, until the shape deviation of a compensation element, which is calculated from the selected points, in its shape deviation falls below a previously established limit value.

According to the invention, the evaluation of measuring points that were measured with computer tomography is ensured by the simulation of a tactile or optical measurement on the point cloud.

The invention also proposes that, for the correction of measurement errors in the tomography, the deviation between the tomographic measurement and the optical or tactile measurement is determined for a first sample part, and this deviation is then used for the correction of the tomographic measurement results.

It can also be provided for the deviation value between tomographic and tactile or optical measurement to be added in memory to the coordinates of the tactile or optical measurements, and corrected during the later evaluation.

The possibility also exists that, in the evaluation of purely tomographically measured parts, the evaluation occurs by the simulation of a tactile or optical measurement on the computer tomography point cloud, taking into account the measurement deviation, which was determined mathematically beforehand, between the tactile/optical and the tomographic measurement for each measuring point.

In particular, the method is characterized by the steps:
1st Step:
   measurement of a first measured object by means of computer tomography,
   measurement of measuring points on the same measured object with tactile or optical sensor,
   storage of the tactile/optical measuring point coordinates with the associated deviation between tactile/optical and tomographically determined measurement result, and evaluation,
2nd Step:
   measurement of a second measured object with similar geometry by means of the tomographic sensor,
   determination of simulated tactile or optical measuring points by selecting one or more tomography measuring points in the vicinity of the place which was stored for the tactile or optical measurement,
   correction of the measurement result so obtained, by the measurement deviation determined in step 1 for the tactile measurement place, and
   evaluation.

The possibility exists to carry out the evaluation of the measurement results by a comparison of the ACTUAL measurement values with CAD target elements, and a color deviation representation.

The evaluation of the measurement results can also be carried out by determining measures, such as length, angle, diameter, distance, and comparison with the target value established in a drawing.

The possibility exists here to obtain target values, upper and lower tolerances, from a CAD format.

An inventive embodiment provides a method for recording parts for the X-ray tomography, where the part to be measured is applied only on spatially small-size contact points of a like-like structure.

The possibility exists here for the application structure with the knobs to be manufactured as a plastic injection molded part.

Moreover, for the evaluation of the X-ray tomography, an erosion filter can be used for separating the knob structures from the measured object proper.

The possibility exists here to use the object size filter to leave only the largest measured object in the image, and thus the knob structures are erased.

Here, the measurements can be carried out on the remaining largest object.

The possibility also exists to connect the measured object and the knob structure by a thin adhesive film, for example one that is applied by spraying Additional details, advantages and characteristics of the invention result not only from the claims, and the characteristics that can be obtained from them—taken separately and/or in combination—, but also from the following description of preferred embodiment examples that can be taken from the drawing.

Figure 1:
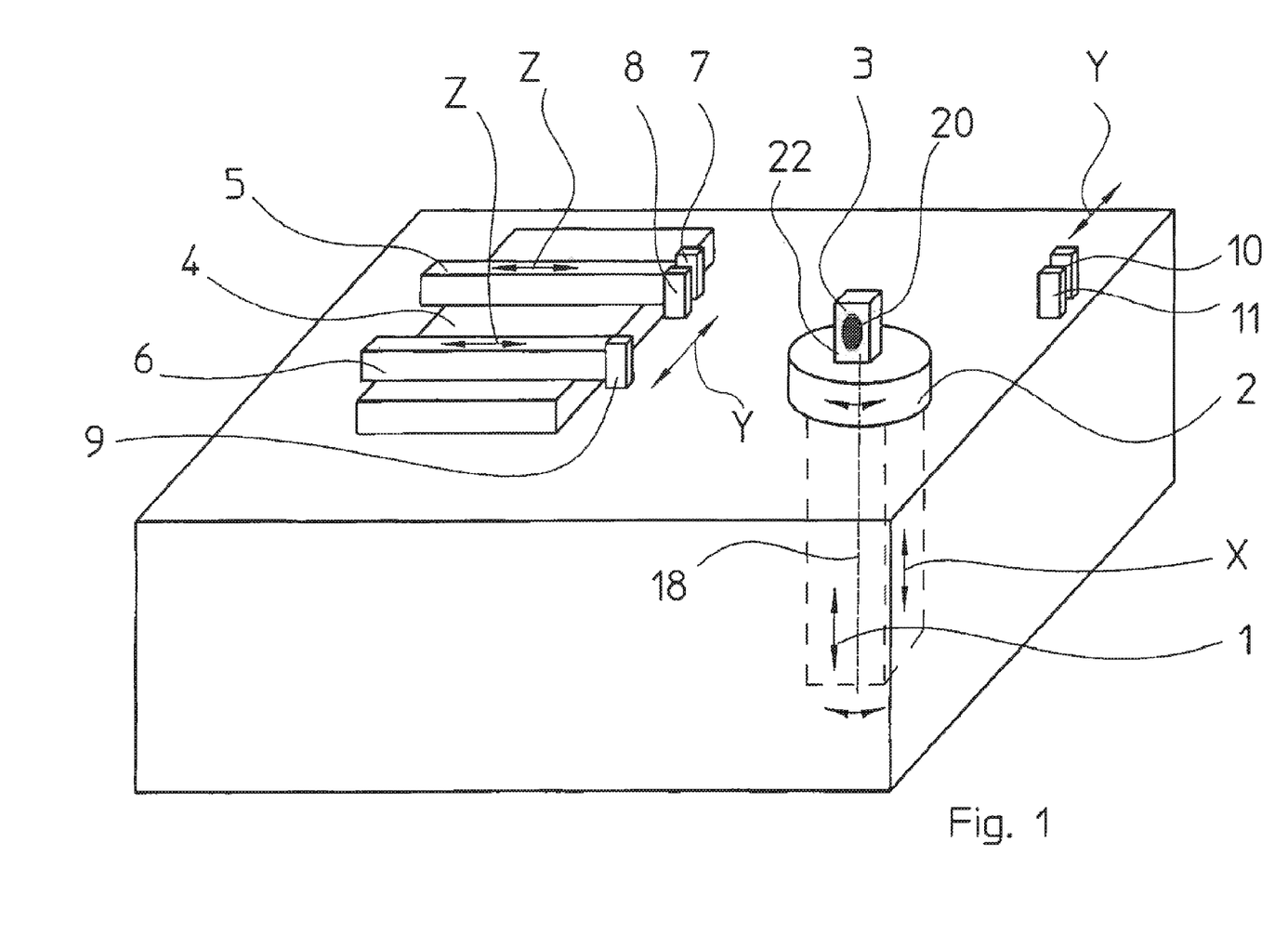
FIG. 1 shows a schematic diagram of a multisensor coordinate measuring device.

In the drawing:

FIG. 1 is a schematic diagram of a multicenter coordinate system intended for the combined use of an X-ray sensor system, including computer tomography, and an optical and tactile sensor system. As optical sensor system, one can consider using here particularly a laser line sensor, although this does not limit the teaching of the invention.

On an axle 18 that runs parallel to the X axis of the coordinate measuring device, a rotating table 2 is arranged. On the latter, a measured object 3 is located, which can thus be rotated about the rotation axis 18, and shifted in the X direction by the axle 18 (double arrow). On a slide 4 that runs parallel to the Y axis, two axles 5, 6 that run parallel to the Z axis are arranged. A sensor 7 for X-ray radiation and a laser line sensor 8 are located on the mechanical axle 5. A tactile sensor 9 is located in addition on the mechanical axle 6. Opposite the X-ray sensor 7, an X-ray source 10 is arranged, which can either be movable in the Y direction, or attached in a fixed manner. Opposite the image processing sensor system 8, a transmitted light source 11 is located. The mechanical axles and slides, respectively, which run along the X, Y or Z axis of the coordinate measuring device, are arranged in such a way that the sensors installed in or on the coordinate measuring device cover in each case the entire measurement area on the rotating table 2.

By the integration of computer tomography (CT) in a multisensor coordinate measuring device, entirely new possibilities are generated. A rapid, noninvasive complete measurement with tomography is combined with highly precise measurements of function measures with a tactile or optical sensor system. Here, according to the invention, the X-ray sensor system (sensor, radiation source) corresponding to the second sensor system (for example, image processing sensor, transmitted or incident light source or tactile sensor optionally with associated image processing system) can be positioned in the coordinate measuring device so that the X-ray sensor system is arranged in an equivalent way to the second sensor system. Here, the X-ray sensor system can be arranged with at least the tactile sensor system and/or the optical sensor system on a common mechanical axle or on a separate mechanical axle, which works analogously to the mechanical axles for the tactile and/or optical sensor system.

From the schematic diagram of FIG. 1, it is apparent that the measured object 3 presents a core 20 which is surrounded by a sheath 22. The core 20 here consists of a heavy material, such as a metal, and the sheath 22 of a lighter material, such as, a plastic. Regardless of the use of the tomography, according to the invention, the possibility also exists to measure the sheath or the shell 22. This is done by measuring a second point cloud with a laser line sensor 8, in addition to the measurement with tomography, i.e., by means of the computer tomography sensor 7, 10. Alternatively to the laser line sensor 8, the tactile sensor 9 or another sensor that is suitable for coordinate measuring devices, can be used, which provides the possibility for tactile sensing of the surface of the measured object 3, i.e., the sheath 22.

Due to the overlap of the computer tomography measurement data of the core 20 and of the measurement data of the surface, i.e., the sheath 22, which are determined with the second sensor, such as, the laser line sensor 8, a total measurement result of the measured object 3 which consists of a combination of materials of different densities is obtained. Consequently, the advantage of the measurement of internal geometries by means of computer tomography can be combined with the advantage of the precise measurement of external geometries with the usual sensors used in the coordinate measurement technology.

Figure 2:
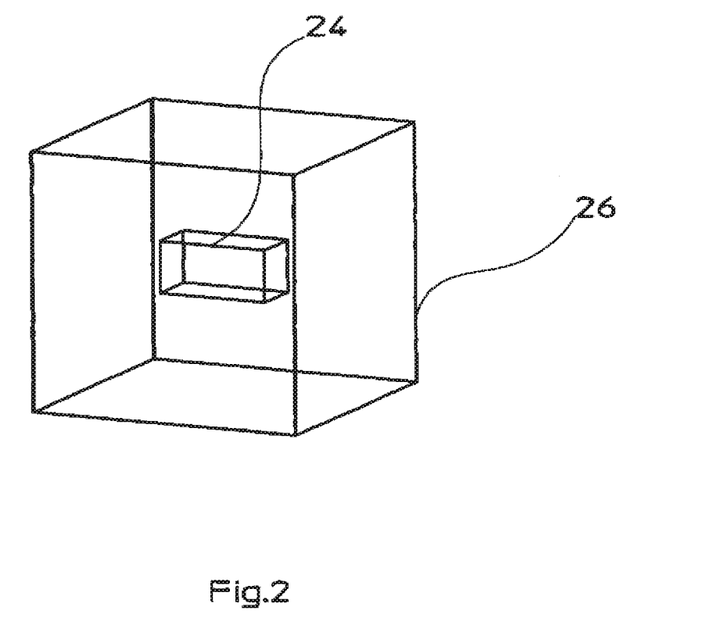
FIG. 2 shows a schematic diagram of a workpiece to be measured.

A workpiece to be measured using the multisensor coordinate measuring device built in accordance with the method of the invention or in accordance with the invention is shown, for example, in FIG. 2. The workpiece presents an inner structure 24 and an envelope or outer structure 26, where the inner structure 24 can consist, for example, of metal, and the outer structure 26 of plastic.

Figure 3:
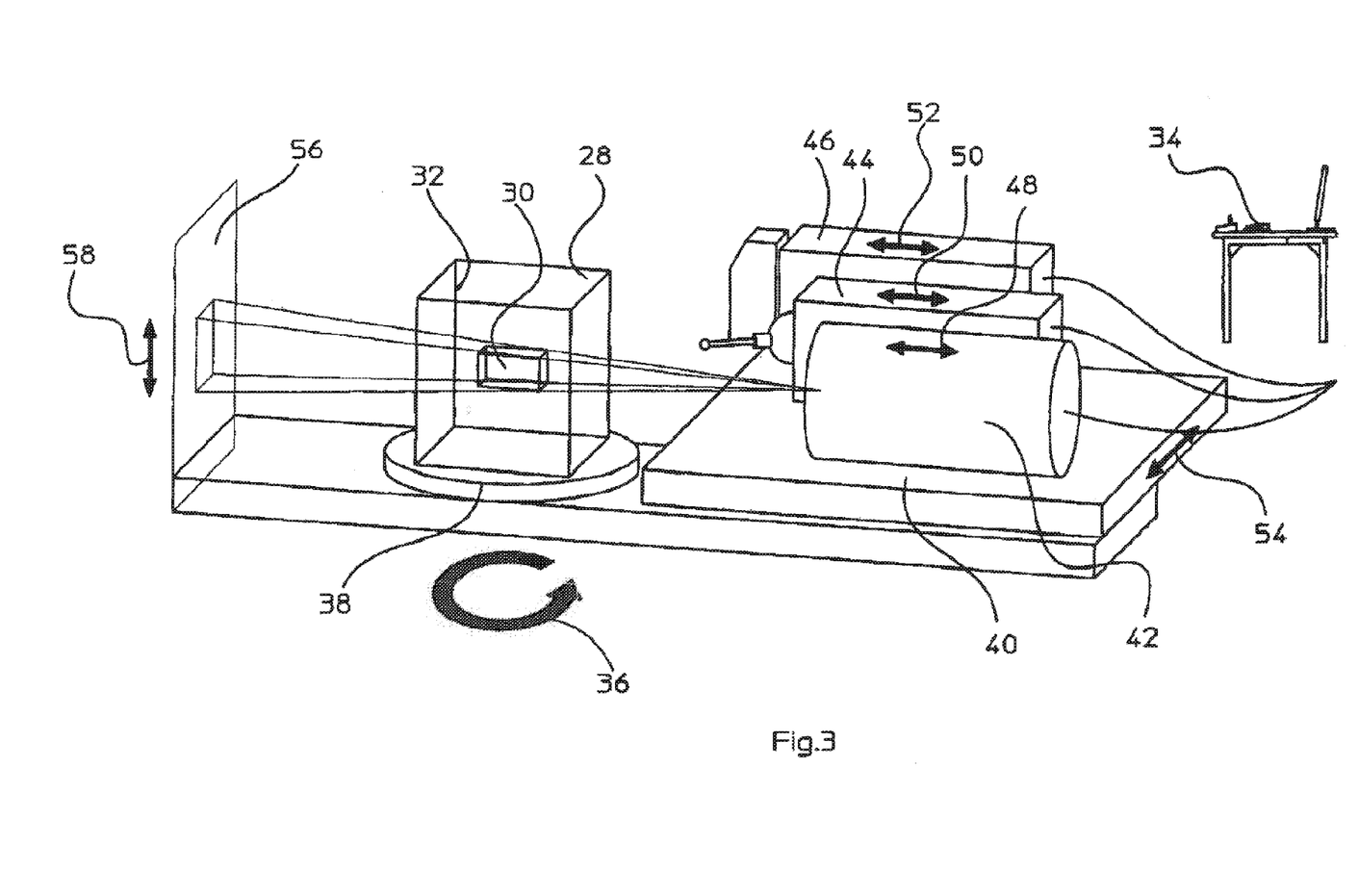
FIG. 3 shows a schematic diagram of a measurement arrangement in which the measurement is carried out with an X-ray detector.
Figure 4:
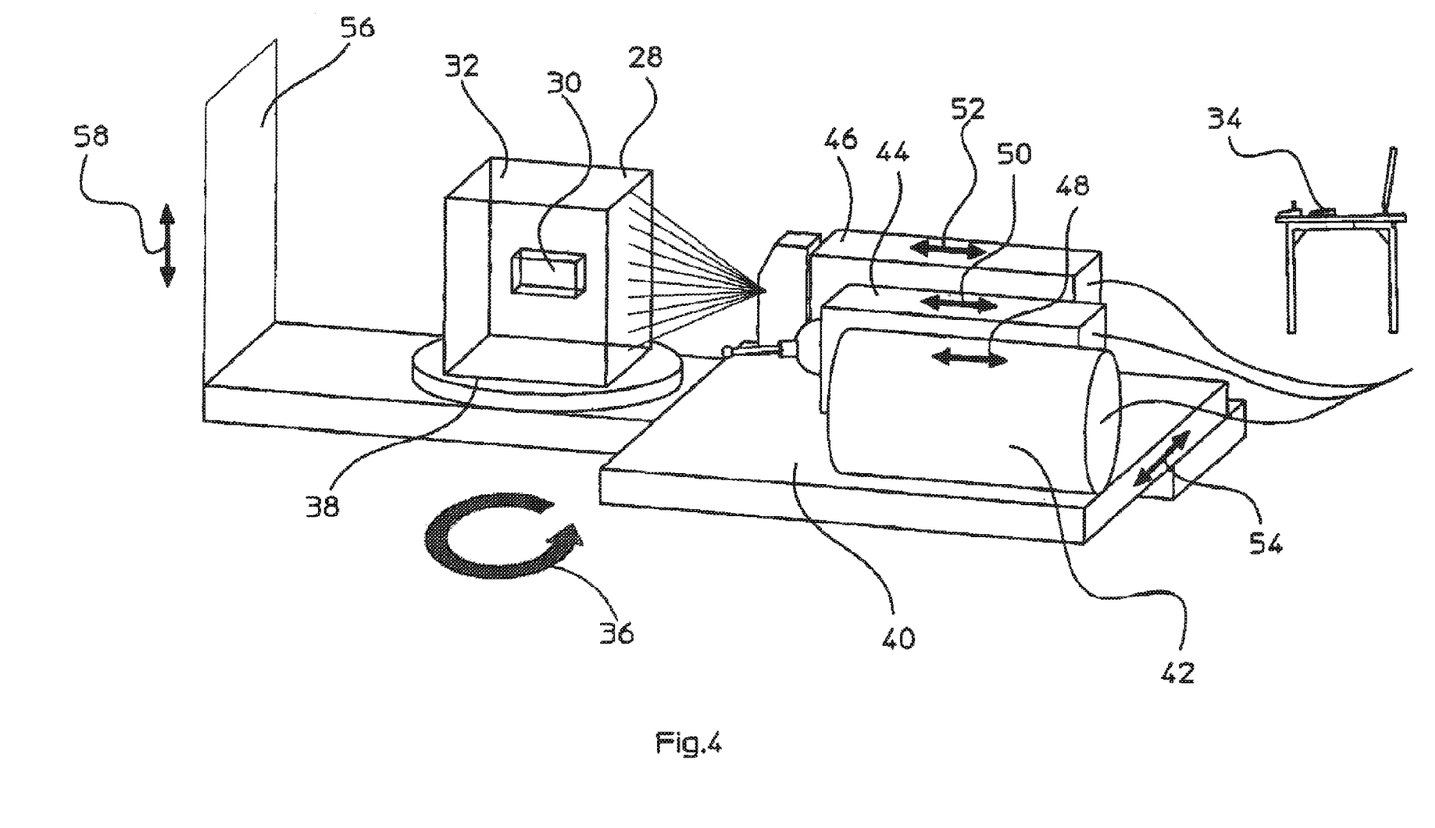
FIG. 4 shows a device corresponding to FIG. 3, where the measurement is carried out with a laser line sensor.
Figure 5:
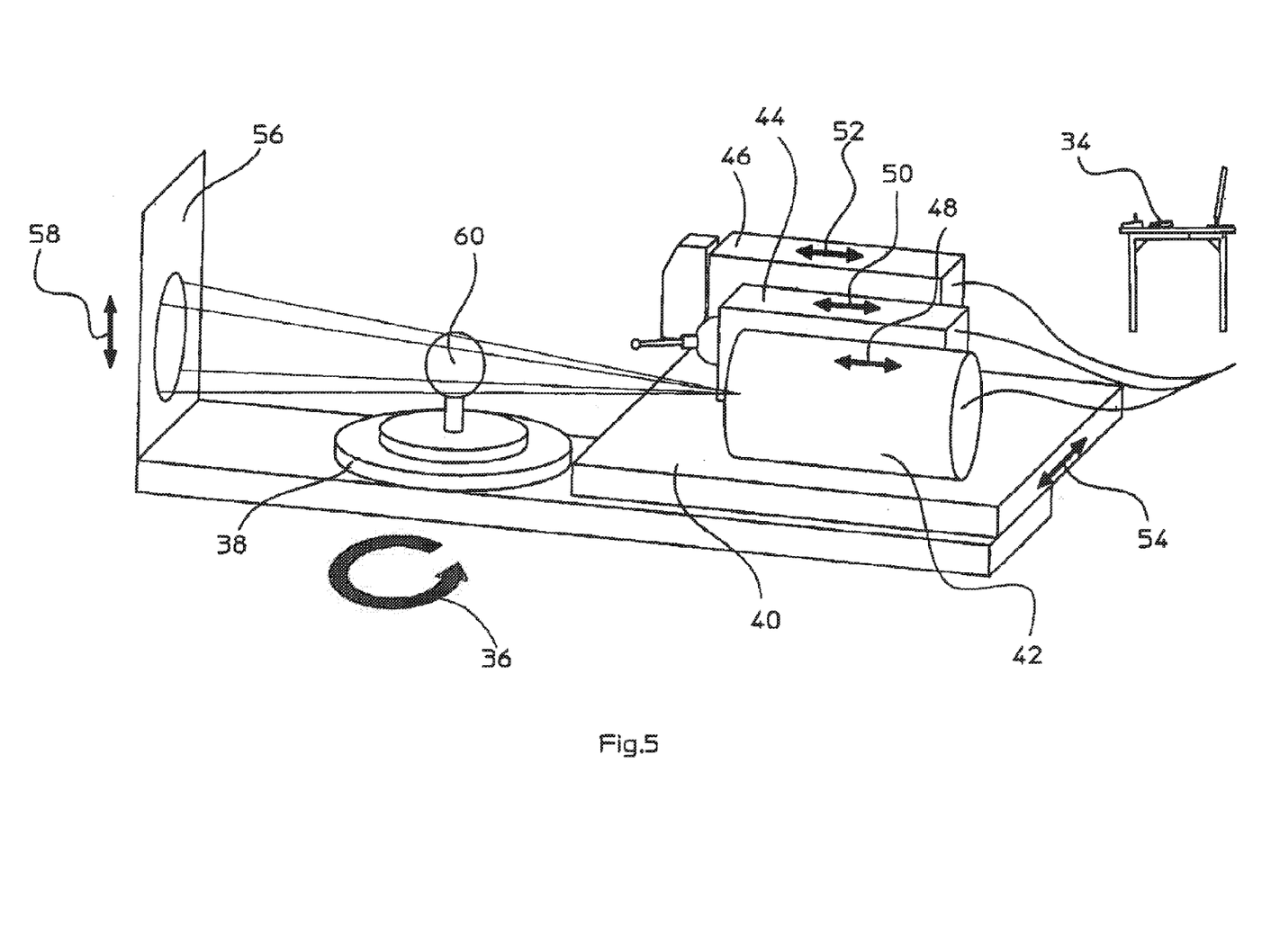
FIG. 5 shows the device according to FIGS. 3 and 4, by means of which the sensors are calibrated.

FIGS. 3-5 show another schematic diagram of a device for complete dimensional measurement of a corresponding workpiece which consists of one or more materials, and which is measured with different sensors. The corresponding workpiece bears the reference numeral 28 in FIGS. 3 and 4, and it presents a core 30 and an envelope 32. The core 30 can be made, for example, of metal, and the envelope 32 of a lighter material, such as, plastic.

The device comprises an evaluation unit 34 with control hardware and software as well as a memory unit for storing measuring points. Furthermore, an input and output unit for an operator is present.

The device comprises a table 38 that can be rotated about a rotation axis (arrow 36) for the workpiece 28. On a carrier 40, an X-ray sensor 42 as well as, as an example, a tactile sensor 44 and a laser line sensor 46 are arranged, which can be shifted along a shifting axes marked by the double arrows 48, 50, 52 on the support 40. The support 40 itself can be shifted along an axis 54 that runs perpendicularly to the adjustment axes 48, 50, 52.

On the side of the workpiece 28 that is located on the opposite with respect to the X-ray sensor 42, an X-ray detector 56 is located, which can adjusted along an axis 58 that runs perpendicularly to the adjustment axes 48, 50, 52, 54. In an additional embodiment, the detector 56 can also be adjusted in the transverse direction, i.e., parallel to the direction 54.

In the embodiment example of FIG. 4, the core or inner structure 30 of the workpiece 28 is detected with the X-ray sensor 42, 56.

In contrast, in FIG. 3, the outer structure, i.e., the sheath 32 of the workpiece 28 is measured, in this case by means of the laser line sensor 46.

For the mutual calibration of the different sensors 42, 44, 46, a reference body 60 is arranged on the rotating table 38 and measured according to FIG. 5. In the embodiment example, the reference body is a sphere of known dimension. The sphere 60 is then measured with the different sensors 42, 44, 46.

A variant of the invention makes it possible to measure multiple points, for example, with computer tomography or the laser line sensor system. This is achieved according to the invention by an appropriate point selection by the connection of the measurement system with CAD data. Thus, software can be implemented which gives the operator the capacity to select an area by the selection of a patch (surface) in a CAD model. By appropriate software algorithms, from all the points of the measured object that are determined by tomography or another sensor system, those that are associated geometrically with this patch are selected. From this, the actual measurement result of the object to be measured is determined. As patch, one can use, for example, a plane or cylinder surface.

Figure 6:
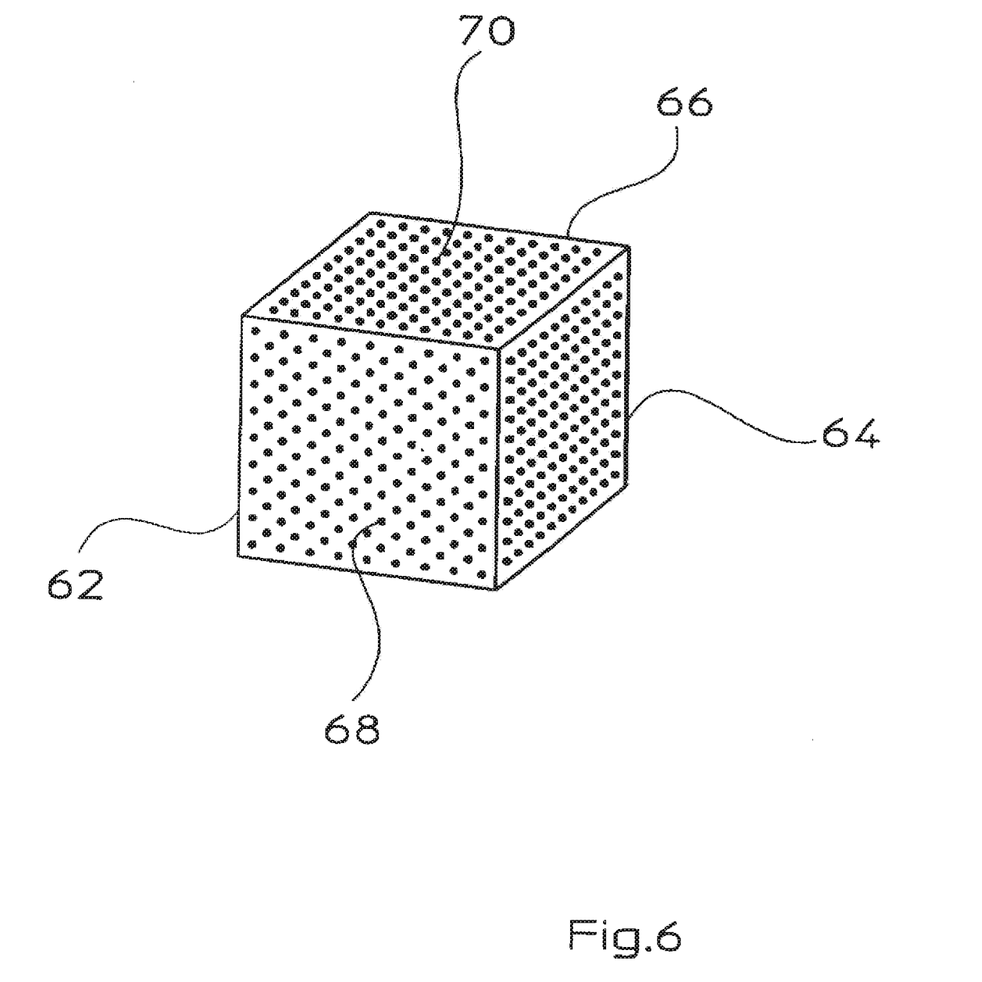
FIG. 6 shows a CAD model.

FIG. 6 is a purely schematic representation of a CAD model with CAD patches (surfaces) 62, 64, 66 (for example, the visible surfaces of the represented cube) as well as a measuring point cloud (black points) 68 consisting of individual 3D measuring points. In the embodiment example, the patch 66 (cube cover surface) is selected, and the points 70 present in the cover surfaces are selected automatically from the overall point cloud 68, and used for further processing, such as, for example, for the calculation of a compensation plane. One can proceed analogously with other cube surfaces. By establishing a mutual relation between the compensation planes, it is possible to calculate angles or separations, for example.

The invention claimed is:

1. Method for dimensional measurement of a measuring object with a coordinate measuring device having an integrated computer tomography sensor,
wherein measuring points to be chosen from all points measured with the computer tomography sensor are selected by the operator by selection of CAD-patches of a CAD-model of the measuring object.

2. Method according to claim 1, characterized in that the measurement of structures that are located inside the component to be measured, is carried out with computer tomography, the measurement of the component surface is carried out completely or partially by optical or tactile sensors and the measurement results of the two sensors are evaluated finally in a coordinate system.

3. Method according to claim 1, characterized in that the sensors used, that is the computer tomography sensor and the optical or tactile or laser line sensor, are mutually calibrated before the measurement with respect to calibration ranges.

4. Method according to claim 1, characterized in that the point clouds measured by tomography and a tactile or optical sensor, are mutually aligned or superposed, by means of optimal overlap of common geometry features, and thus a measurement within a coordinate system becomes possible.

5. Method according to claim 1, characterized in that the CAD model of the measured object and the measuring point cloud are made to overlap by BestFit or manual adaptation.

6. Method according to claim 1, characterized in that all the measuring points that are located within a search area about the chosen CAD patch are used for the further evaluation.

7. Method according to claim 1, characterized in that, in the case of the selection of individually measured points, additional points are automatically selected and added.

8. Method according to claim 1, characterized in that, before the selection of a point, a regular geometric element, such as, a cylinder/plane is selected as target element, and then as many measuring points are selected by the software as are needed, until the shape deviation of a compensation element of the type of the target element, which is calculated from the selected points, in its shape deviation falls below a previously established limit value.

9. Method according to claim 1, characterized in that, before the selection of a point, a cylinder is selected as regular geometric target element, and then as many measuring points are selected by the software as are needed, until the shape deviation of a compensation element, which is calculated from the selected points, in its shape deviation falls below a previously established limit value.

10. Method according to claim 1, characterized in that, before the selection of a point, a plane is selected as regular geometric target element, and then as many measuring points are selected by the software as are needed, until the shape deviation of a compensation element, which is calculated from the selected points, in its shape deviation falls below a previously established limit value.

11. Method according to claim 1, characterized in that, before the selection of a point, a sphere is selected as regular geometric target element, and then as many measuring points are selected by the software as are needed, until the shape deviation of a compensation element, which is calculated from the selected points, in its shape deviation falls below a previously established limit value.

12. Method according to claim 1, characterized in that, before the selection of a point, a torus is selected as regular geometric target element, and then as many measuring points are selected by the software as are needed, until the shape deviation of a compensation element, which is calculated from the selected points, in its shape deviation falls below a previously established limit value.

13. Method according to claim 1, characterized in that, before the selection of a point, a target element in the form of a free form patch described in the CAD format is selected, and then as many measuring points are selected by the software as are needed, until the shape deviation of a compensation element, which is calculated from the selected points, in its shape deviation falls below a previously established limit value.

14. Method according to claim 1, characterized in that the evaluation of measuring points measured with computer tomography is ensured by the simulation of a tactile or optical measurement on the point cloud.

15. Method according to claim 1, characterized in that, for correcting measurement errors in the tomography, the deviation between the tomographic measurement and the optical or tactile measurement is determined for a first sample part, and this deviation is then used for correcting the tomographic measurement results.

16. Method according to claim 1, characterized in that, the deviation value between tomographic and tactile or optical measurement is added in memory to the coordinates of the tactile or optical measuring points, and corrected during the later evaluation.

17. Method according to claim 1, characterized in that, in the evaluation of purely tomographically measured parts, the evaluation by simulation of a tactile or optical measurement on the computer tomography point cloud is carried out taking into account the measurement deviation between the tactile/optical and the tomographic measurement which was determined mathematically beforehand for each measuring point.

18. Method according to claim 1, characterized by
step 1:
measurement of a first measured object by means of computer tomography,
measurement of measuring points on the same measured object with tactile or optical sensor,
storage of the tactile/optical measuring point coordinates with the associated deviation between tactile/optical and tomographically determined measurement result, and
evaluation,
step 2:
measurement of a second measured object with similar geometry by means of the tomographic sensor,
determination of simulated tactile or optical measuring points by selecting one or more tomography measuring points in the vicinity of the place which was stored for the tactile or optical measurement,
correction of the measurement result so obtained, by the measurement deviation determined in step 1 for the tactile measurement place, and
evaluation.

19. Method according to claim 1, characterized in that the evaluation of the measurement results is carried out by comparing the actual measurement values with the CAD target elements, and a color deviation representation.

20. Method according to claim 1, characterized in that the evaluation of the measurement results is carried out by determining measures, such as length, angle, diameter, distance, and comparison with the target values established in a drawing.

21. Method according to claim 1, characterized in that target values, the upper and lower tolerances, are taken from a CAD format.

22. Method according to claim 1, characterized in that, to record with X-ray tomography parts to be measured, part to be measured must be applied on spatially small-size contact points of a like-like structure.

23. Method according to claim 1, characterized in that the application structure with the knobs is manufactured as a plastic injection molded part.

24. Method according to claim 1, characterized in that, for the evaluation of the X-ray tomography, an erosion filter is used for separating the knob structures from the measured object proper.

25. Method according to claim 1, characterized in that, by means of an object size filter, only the largest measured object remains in the image, and thus the knob structures are erased.

26. Method according to claim 1, characterized in that the measurements are carried out on the remaining largest object.

27. Method according to claim 1, characterized in that the measured object and knob structure are connected by a thin adhesive film, for example one that is applied by spraying.

28. Coordinate measuring device for measuring an object (3, 28, 30, 32) with an X-ray sensor system as first sensor system comprising an X-ray radiation source (10, 42) and at least an X-ray radiation sensor that captures the X-rays (7, 56), as well as a second sensor system, such as a tactile and/or optical sensor system (8, 11; 9, 44, 46), is adapted for positioning in the x, y and/or z direction of the coordinate measuring device relative to the object, where the X-ray sensor system (7, 10, 42, 56) is adapted for positioning in accordance with the second sensor system (8, 11; 9, 44, 46) in the coordinate measuring device (10),
wherein said object (28) consists of a core (20, 30) with a first density and an envelope (22, 32) with a second density, the first density is much higher than the second density, the core is measurable with the X-ray sensor system (7, 10, 42, 56), and the envelope with the second sensor system (8, 9, 11, 44, 46), and wherein the object to be measured (3, 28) is applied on spatially small-size contact points of a knob-like structure.

29. Coordinate measuring device according to claim 28, characterized in that the coordinate measuring device comprises an evaluation unit (34), in which the measurement results of the two sensors can be evaluated finally in a common coordinate system.

30. Coordinate measuring device according to claim 28, characterized in that the second sensor system (8, 46) is a laser line sensor.

31. Coordinate measuring device according to claim 28, characterized in that the second sensor system is a tactile sensor (9, 44).

32. Coordinate measuring device according to claim 28, characterized in that the application structure with the knobs is a plastic injection molded part.

33. Coordinate measuring device according to claim 28, characterized in that, for the evaluation of the X-ray tomography, an erosion filter for separating the knob structures from the measured object proper is provided.

34. Coordinate measuring device according to claim 28, characterized in that, due to the use of an object size filter, only the largest measured object remains in the image, and thus the knob structures are erased.

35. Coordinate measuring device according to claim 28, characterized in that the measurements can be carried out on the remaining largest object.

36. Coordinate measuring device according to claim 28, characterized in that the measured object and the knob structure are connected by a thin adhesive film, for example one that is applied by spraying.

* * * * *